US011524160B2

(12) United States Patent
Sharma et al.

(10) Patent No.: US 11,524,160 B2
(45) Date of Patent: Dec. 13, 2022

(54) CONTROL OF FUNCTIONAL ELECTRICAL STIMULATION USING MOTOR UNIT ACTION POTENTIALS

(71) Applicant: Battelle Memorial Institute, Columbus, OH (US)

(72) Inventors: Gaurav Sharma, Lewis Center, OH (US); Samuel Colachis, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 120 days.

(21) Appl. No.: 16/913,706

(22) Filed: Jun. 26, 2020

(65) Prior Publication Data

US 2020/0406035 A1 Dec. 31, 2020

Related U.S. Application Data

(60) Provisional application No. 62/868,317, filed on Jun. 28, 2019.

(51) Int. Cl.
*A61N 1/36* (2006.01)
*G16H 40/63* (2018.01)
*A61N 1/04* (2006.01)

(52) U.S. Cl.
CPC ....... *A61N 1/36031* (2017.08); *A61N 1/0452* (2013.01); *A61N 1/0484* (2013.01); *A61N 1/36003* (2013.01); *G16H 40/63* (2018.01)

(58) Field of Classification Search
CPC .............. A61N 1/0484; A61N 1/36003; A61N 1/0456; A61N 1/0452
See application file for complete search history.

(56) References Cited

U.S. PATENT DOCUMENTS

2012/0022347 A1* 1/2012 Liu ................... A61B 5/14532
600/587
2012/0172682 A1* 7/2012 Linderman .......... A61B 5/6806
600/301

(Continued)

FOREIGN PATENT DOCUMENTS

WO WO 2016/196797 A1 12/2016

OTHER PUBLICATIONS

International Search Report for PCT Application No. PCT/US2020/039809 dated Sep. 16, 2020.

*Primary Examiner* — Michael J D'Abreu
(74) *Attorney, Agent, or Firm* — Fay Sharpe LLP (57) ABSTRACT

A therapeutic or diagnostic device comprises a wearable electrodes garment including electrodes disposed to contact skin when the wearable electrodes garment is worn, and an electronic controller operatively connected with the electrodes. The electronic controller is programmed to perform a method including: receiving surface electromyography (EMG) signals via the electrodes and extracting one or more motor unit (MU) action potentials from the surface EMG signals. The method may further include identifying an intended movement based at least on features representing the one or more extracted MU action potentials and delivering functional electrical stimulation (FES) effective to implement the intended movement via the electrodes of the wearable electrodes garment. The method may further include generating a patient performance report based at least on a comparison of features representing the one or more extracted MU action potentials and features representing expected and/or baseline MU action potentials for a known intended movement.

19 Claims, 9 Drawing Sheets

(56) References Cited

U.S. PATENT DOCUMENTS

2017/0312576 A1 11/2017 Natarajan
2019/0091472 A1 3/2019 Friedenberg

* cited by examiner

| | MUs | PNR (dB) | Mean firing rate (pps) | ISI variability (%) |
|---|---|---|---|---|
| Index | 5 | 34.58±2.57 | 13.50±6.56 | 38.71±18.24 |
| Middle | 3 | 32.86±5.42 | 14.21±3.60 | 35.63±5.56 |
| Ring | 3 | 30.36±3.84 | 14.70±5.97 | 27.63±12.53 |
| Pinky | 3 | 44.23±1.64 | 11.05±8.61 | 31.25±13.08 |
| Thumb | 1 | 45.30 | 11.52 | 32.69 |
| Elbow Flexion | 5 | 34.56±3.62 | 15.56±5.41 | 54.79±20.71 |
| Wrist Flexion | 7 | 31.10±4.32 | 17.42±3.66 | 43.78±6.72 |
| Wrist Pronation | 4 | 33.70±6.55 | 16.08±4.06 | 39.94±5.57 |

CONTROL OF FUNCTIONAL ELECTRICAL STIMULATION USING MOTOR UNIT ACTION POTENTIALS

CROSS-REFERENCE TO RELATED APPLICATIONS

This application claims priority to U.S. Provisional Patent Application Ser. No. 62/868,317 filed Jun. 28, 2019. U.S. Provisional Patent Application Ser. No. 62/868,317 filed Jun. 28, 2019 is incorporated herein by reference in its entirety.

BACKGROUND

The following relates to the functional electrical stimulation (FES) arts, electromyography (EMG) arts, EMG controlled FES arts, spinal cord injury (SCI) rehabilitation arts, stroke rehabilitation arts, and related arts.

FES devices apply electrical stimulation via surface or intramuscular electrodes in order to stimulate muscle contraction and consequent motion of an arm, leg, hand, or other body part. Use of surface electrodes, as opposed to intramuscular electrodes, is advantageously painless and non-invasive. In the case of a paralyzed patient, that is, a patient having a paralyzed body part due to spinal cord injury (SCI), stroke debilitation, or some other cause of the paralysis, an FES device operatively connected with the paralyzed body portion has the potential to restore volitional control of the hand, forearm, and wrist.

To do so, however, the patient's volitional intent must be measured and converted into FES control signals. One approach is to employ a brain-computer interface (BCI) which measures electrical activity in the motor cortex of the brain via intracortical electrodes, and decodes volitional intent from measured brain electrical activity. This approach has certain disadvantages, notably the invasive nature of the intracortical electrodes and the complexity of brain electrical activity. Even assuming the electrodes are measuring only motor cortex activity, this activity encompasses volitional intent relating to the entire patient's body. This makes decoding volitional intent as respecting a specific body part (e.g., the wrist, or even more precisely a particular muscle of the wrist) challenging. In the case of a stroke patient, effects of the stroke on brain electrical activity may further complicate the decoding of the brain electrical activity.

Certain improvements are disclosed herein.

BRIEF SUMMARY

In accordance with some illustrative embodiments disclosed herein, a therapeutic or diagnostic device comprises a wearable electrodes garment including electrodes disposed to contact skin when the wearable electrodes garment is worn, and an electronic controller operatively connected with the electrodes. The electronic controller is programmed to perform a method including receiving surface electromyography (EMG) signals via the electrodes and extracting one or more motor unit (MU) action potentials from the surface EMG signals. The method may further include identifying an intended movement based at least on feature representing the one or more extracted MU action potentials and delivering functional electrical stimulation (FES) effective to implement the intended movement via the electrodes of the wearable electrodes garment. The method may further include generating a patient performance report based at least on a comparison of features representing the one or more extracted MU action potentials and features representing expected and/or baseline MU action potentials for a known intended movement.

In accordance with some illustrative embodiments disclosed herein, a therapeutic device comprises a wearable electrodes garment including electrodes disposed to contact skin when the wearable electrodes garment is worn, and electronic controller operatively connected with the electrodes. The electronic processor is programmed to perform a method including: receiving surface EMG signals via the electrodes; extracting one or more MU action potentials from the surface EMG signals; identifying an intended movement based on features including at least features representing the one or more extracted MU action potentials; and delivering FES effective to implement the intended movement via the electrodes of the wearable electrodes garment.

In accordance with some illustrative embodiments disclosed herein, a therapeutic or diagnostic method comprises receiving surface EMG signals via electrodes of a wearable electrodes garment and, using an electronic processor: extracting one or more motor unit (MU) action potentials from the surface EMG signals; and one of (i) identifying an intended movement based at least on the one or more extracted MU action potentials delivering functional electrical stimulation (FES) effective to implement the intended movement via the electrodes of the wearable electrodes garment or (ii) generating a patient performance report based at least on a comparison of the one or more extracted MU action potentials and expected and/or baseline MU action potentials for a known intended movement.

BRIEF DESCRIPTION OF THE DRAWINGS

Any quantitative dimensions shown in the drawing are to be understood as non-limiting illustrative examples. Unless otherwise indicated, the drawings are not to scale; if any aspect of the drawings is indicated as being to scale, the illustrated scale is to be understood as non-limiting illustrative example.

DETAILED DESCRIPTION

Another possible approach for measuring volitional intent for driving functional electrical stimulation (FES) is to measure electromyography (EMG) signals at the paralyzed wrist (or other paralyzed body portion). EMG signals are electrical activity produced by skeletal muscles. This approach is premised on the hypothesis that, in spite of the SCI or cause of the paralysis, the patient's volitional intent still generates neural signals to the muscles of the paralyzed body portion, albeit at insufficient strength to stimulate functional muscle contraction. The likelihood of this hypothesis is arguably greater in the case of a stroke patient as compared with an SCI patient; however, experiments have demonstrated that the hypothesis holds for some SCI patients.

However, employing EMG signals for volitional FES control is challenging. If EMG signals are present at all in the paralyzed body part, they are expected to be greatly attenuated compared with EMG signals in a healthy person. This might be countered to some degree by use of intramuscular electrodes (e.g. needle electrodes) to measure the EMG signals, but invasive intramuscular electrodes are often unacceptable to the patient in the case of a wrist, arm, or other flexing body part. Surface EMG signals can be measured using electrodes contacting the skin, which may be more acceptable to the patient. However, the surface EMG signals are weaker than intramuscular EMG signals (and, as noted, the EMG signals are already expected to be greatly attenuated in the paralyzed body part due to the paralysis). A still further difficulty is that the EMG signals can be difficult to decode, as they are not direct metrics of volitional intent but rather are a measure of muscular activity stimulated by the volitional intent. The muscular contractions producing the EMG signals in a paralyzed body part may not simply be attenuated versions of the intended muscular contractions, but instead may include involuntary tremors or other non-volitional muscle activity.

It is recognized herein that measuring motor unit (MU) action potentials provide additional information that can be used in addressing the above-mentioned difficulties. A motor unit is the combination of a motor neuron and the skeletal muscle fibers innervated by that motor neuron. The MU action potential is the electrical signal carried by the motor neuron. Hence, the MU action potential directly captures the volitional intent of the paralyzed patient (albeit likely attenuated due to the paralysis).

The volitional intent to perform a movement of a body part translates, at the MU level, into various parameters such as (in the illustrative examples): (i) the number of MUs recruited to perform the movement; and (ii) the discharge rate (aka firing rate, pulse rate) of the recruited motor units. The number of distinct MU action potentials is extracted by Convolutional Kernel Compensation (CKC) decomposition which has been shown to be effective to extract MU action potentials. See, e.g. Holobar et al., "Accurate identification of motor unit discharge patterns from high-density surface EMG and validation with a novel signal-based performance metric", J. Neural Eng., vol. 11, no. 1, p. 016008, February 2014. The CKC decomposition thus yields the number of MUs recruited as the number of distinct extracted MU action potentials. Other techniques for extracting the MU action potentials are also contemplated, such as wavelet decomposition. Analysis of the discharge pattern of each distinct MU action potential provides information about discharge rate for that MU. More particularly, in the illustrative examples the discharge rate is characterized as a "mean firing rate" or "mean discharge rate" in pulses per second (pps). Additionally, the discharge pattern of each MU action potential is characterized in the illustrative examples by an Interpulse Interval (ISI) variability which is the average ISI of the MU divided by the ISI standard deviation for the MU, in a percentage value. High ISI variability may be an indication of synaptic noise. As a further quality metric, the Pulse-to-Noise Ratio (PNR) in dB is computed for the discharge pattern.

It is recognized herein that effective FES control advantageously relies upon both electromyography (EMG) signals and the MU action potentials extracted as described above. Although EMG signals may not unambiguously correlate with the patient's volitional intent in detail (for example, due to involuntary tremors which also induce EMG signals), it is reasonable to expect that EMG signals will predominantly arise from the muscles that the patient intends to contract. For example, if the patient's volitional intent is to move the index finger, then the EMG signals should predominantly arise from the index finger, and not (for example) from the thumb.

On the other hand, once regions of high neural activity have been identified, this serves as prior knowledge for analyzing the MU action potentials to more precisely decode the particular type of movement that is intended by the patient. For example, a small number of MU action potentials (corresponding to a small number of recruited MUs) and a low discharge rate for those MU action potentials suggests the patient intends to perform a precisely controlled but low force action. Conversely, a high number of MU action potentials with high discharge rates suggests the patient intends to perform a coarse movement with a larger force. Hence, for example, if the EMG decoding indicates the patient intends to move the index finger and the number of MU action potentials is low and have low discharge frequencies, it may be determined that the patient intends to lightly tap something with the index finger; whereas, if the EMG decoding indicates the patient intends to move the index finger and the number of MU action potentials is high and have high discharge frequencies, it may be determined that the patient intends to strongly grasp something using the index finger. The MU actions potential features can be used instead of, or together with, decoded EMG signals for identifying the type and force of movement intended by the patient.

Figure 1:
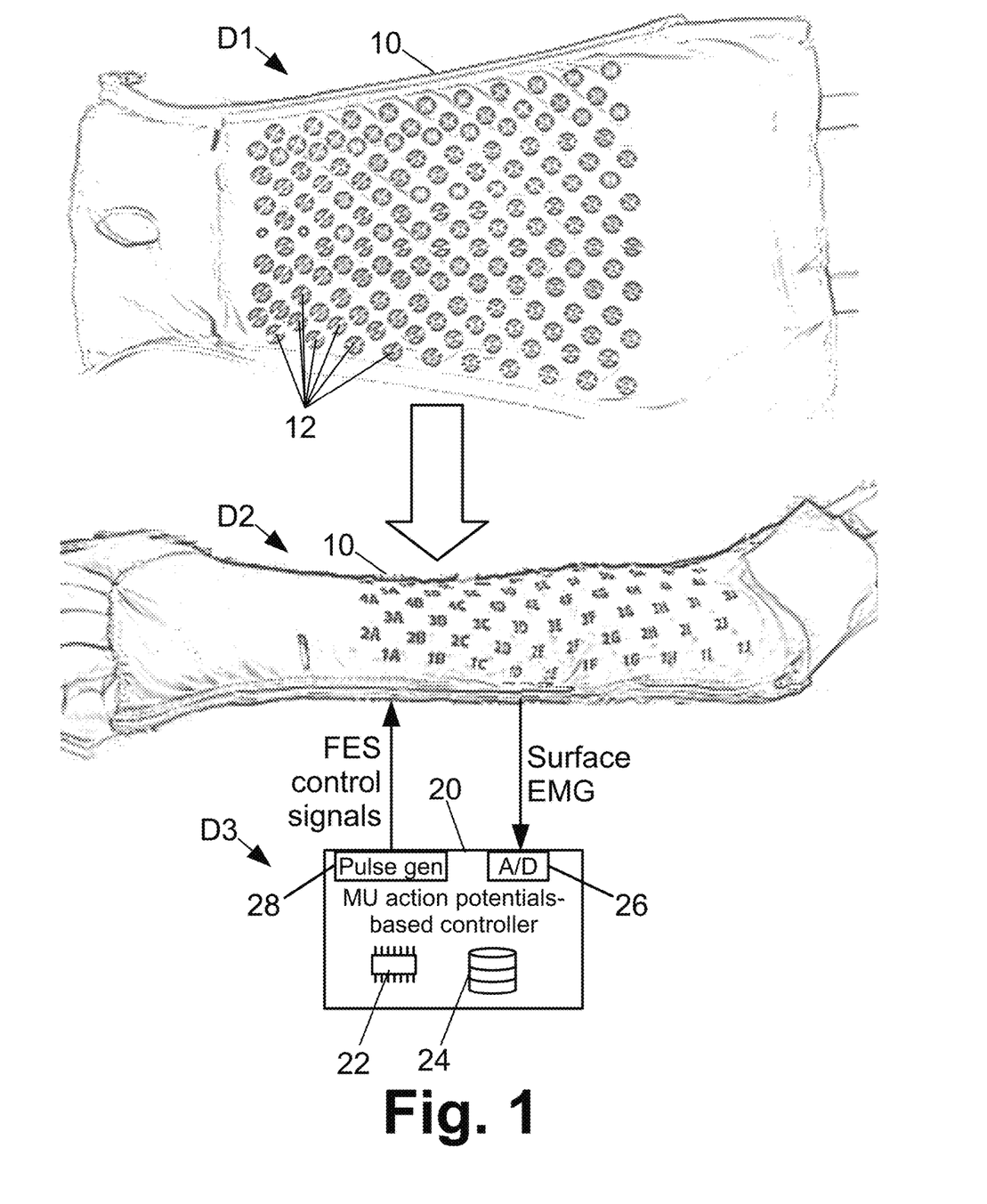
FIG. 1 diagrammatically illustrates a functional electrical stimulation (FES) system.

With reference to FIG. 1, an illustrative wearable electrodes garment 10 comprises a sleeve designed to be worn around the forearm of a patient. The electrodes sleeve 10 is shown unwrapped with the side that contacts the forearm in view in the upper drawing D1 of FIG. 1. This view reveals an array of surface electrodes 12 that contact the skin to measure surface potentials on the skin of the forearm. The illustrative embodiment includes 150 electrodes, which are 12 mm diameter stainless steel discs with an interelectrode distance of approximately 15 mm, spanning from the wrist to the elbow joint. This is merely an illustrative layout; in general, the number of electrodes may vary, e.g. 160 electrodes may be used for a larger-size sleeve, or fewer than 150 electrodes may be used for a smaller sized sleeve, or more or fewer electrodes may be used in a sleeve of a given size to provide higher or lower spatial resolution, respectively. Similarly, the mentioned size and specific manufacture of the electrodes is merely a nonlimiting illustrative example. In general, the electrodes should be distributed over the skin contacted by the garment 10 with sufficient number and density to provide high density EMG (HDEMG) measurements at least in regions for which HDEMG measurements are desired. Typically, it is expected that the garment will include at least 50 electrodes to provide HDEMG measurements, although fewer than 50 electrodes is also contemplated. In general, any type of electrode suitable for electrocardiography (ECG), electromyography (EMG), electroencephalography (EEG), or the like can be employed to measure the surface potentials. The middle drawing D2 of FIG. 1 illustrates the electrodes sleeve 10 wrapped onto a forearm of a patient. In this view the electrodes 12 are not visible as they are contacting the skin of the forearm. (However, as seen in the middle drawing D2, the illustrative electrodes sleeve 10 includes two-character digit-letter designators of the underlying electrodes. These designators are optional). It is to be understood that while a forearm sleeve is illustrated, the wearable electrodes garment is suitably configured to be worn on the anatomical body part for which EMG signals are to be detected and/or FES support is to be delivered (e.g. forearm, wrist, hand, leg, ankle, various combinations thereof, and/or so forth). A wrap-around (or otherwise wearable) electrodes garment such as the wrap-around forearm electrodes sleeve 10 of FIG. 1 advantageously can be designed to fit patients of various forearm sizes (and possibly even legs); however, for improved comfort it is contemplated to employ a fitted sleeve, sock, or the like that may not be of a wrap-around design but that is fitted or sized for the particular patient. In the description herein, the term "paralyzed" body part may sometimes be employed as a designation of the body part on which the electrodes garment is worn; however, the term "paralyzed" should be understood to encompass a partially paralyzed body part or a body part that has some motion but not well controlled motion, for example such as may be the case for stroke debilitation.

By way of further non-limiting illustration, some suitable embodiments of the wearable electrodes garment 10 including the electrodes 12 are described in Bouton et al., U.S. Pat. No. 9,884,178 issued Feb. 6, 2018 and Bouton et al., U.S. Pat. No. 9,884,179 issued Feb. 6, 2018, both of which are incorporated herein by reference in their entireties.

With continuing reference to FIG. 1, the lower drawing D3 shows a motor unit (MU) action potentials based electronic controller 20 receives surface EMG signals from the electrodes 12 of the electrodes sleeve 10, and generates FES control signals delivered to the electrodes 12 to perform functional electrical stimulation of the forearm (in the illustrative case) or other body part on which the electrodes garment is worn. The controller 20 also preferably removes any FES evoked artifacts that can corrupt the volitional EMG data. These artifacts can be stimulation induced artifacts, as well as M-wave artifacts due to the movement of the FES-activated muscles. The EMG signals may be received, and the FES signals delivered, via electrical conductors implemented as wires, circuitry of a flexible printed circuit board (PCB) or a rigid PCB or combinations thereof, or the like. For example, the electrodes garment 10 may include a flexible PCB (not shown) via which EMG and FES signals are distributed from/to the electrodes 12. Alternatively, wiring may be woven into fabric of the electrodes garment 10, and/or so forth. The PCB(s), wiring, or other circuitry provides separate channels for each electrode 12, so that the surface EMG signal of each electrode can be individually received and a distinct FES signal sent to each individual electrode. In the illustrative example, there are 150 electrodes and a corresponding 150 channels. It is contemplated to have two or more physical electrodes wired to a single channel, for example if the electrodes are smaller than the spatial resolution desired for a certain region of the anatomy—in such a case the two or more commonly wired electrodes are treated as a single electrode. This kind of differential or bipolar mode can also be advantageous to reduce noise. As a further variant, while in the illustrative example the same set of 150 electrodes are used for both reading surface EMG signals and delivering FES (with suitable time domain multiplexing), in an alternative embodiment it is contemplated to have separate sets of interleaved electrodes for reading the surface EMG signals and delivering the FES. It is additionally/alternatively contemplated to employ wireless connections, for example in one alternative arrangement a wireless connection (such as Bluetooth) may be used to connect the electronic controller 20 with the electrodes garment 10 and a flexible PCB secured with or into the garment may be used to distribute signals to/from the electrodes 12.

In one approach, separate independent sets of EMG and FES electrodes across the interface can be used for sensing and stimulation. The method of choosing these separate sets of EMG and FES electrodes may include a personalized mapping or a consistent standardized set of EMG and FES electrode groups. For example, an injured patient may have sparse EMG signal only in certain parts of the given limb (e.g., due to a stroke or other injury). Therefore, the EMG recording electrode locations may need to be personalized to the specific target muscles that emit a sufficient EMG signal. In this scenarios, other electrodes may not be able to record any EMG signal, and can therefore be excluded or used for separate functions. Furthermore, as an example, standardized independent sets of EMG and FES electrodes can have a fixed location sufficient to record the needed EMG signals and stimulate the needed muscles with FES. This can be achieved by leveraging the known gross anatomy of the target muscle's location or another method.

In another approach, overlapping sets of EMG and FES electrodes can be used for sensing and stimulation. For example, on one electrode EMG can be sensed and used to rapidly produce FES on the same electrode or vice versa. Electronics execute suitably fast switching between sense and stimulation modes and prevents system damage or recording signal artifact (i.e., 'EMG mode' vs. 'FES mode'). The two approaches can be combined or used separately using EMG or FES electrodes on separate electrode array interfaces (e.g., multiple devices distributed over separate body parts). For example, two sleeves can be used on both the right and left arm. EMG can be recorded on a sleeve located on the right arm and used to trigger FES located on the left arm.

The term "surface EMG signals" is used herein to denote the electrical surface potentials received via the electrodes 12. It is recognized herein that these "surface EMG signals" are actually a superposition of EMG signals (that is, electrical activity produced by skeletal muscles) and MU activation potentials (that is, electrical signals delivered by motor neurons to the muscles). However, the electrical activity produced by skeletal muscles is much stronger than the MU activation potentials, and hence the electrical activity produced by skeletal muscles is the dominant signal component of the measured surface potentials. Moreover, the surface potentials measured by surface electrodes disposed over musculature are commonly referred to in the literature as "surface EMG signals". Accordingly, that term is used herein, with the understanding that the surface EMG signals also include a lesser component comprising MU activation potentials.

Figure 2:
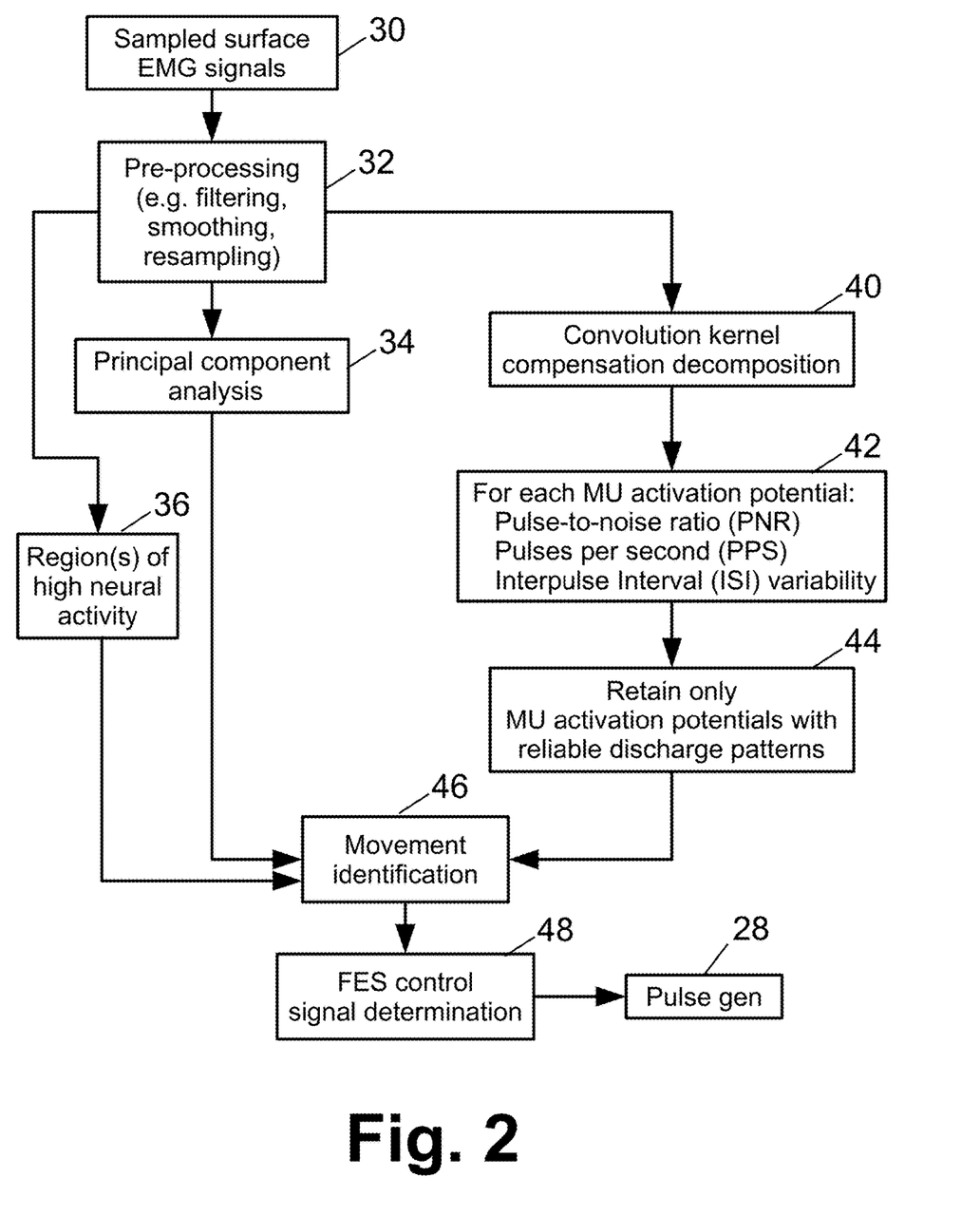
FIG. 2 diagrammatically illustrates a method suitably performed by the controller of the device of FIG. 1 for generating FES signals based on surface potentials measured by the electrodes of the FES from which MU action potentials are extracted.
Figure 3:
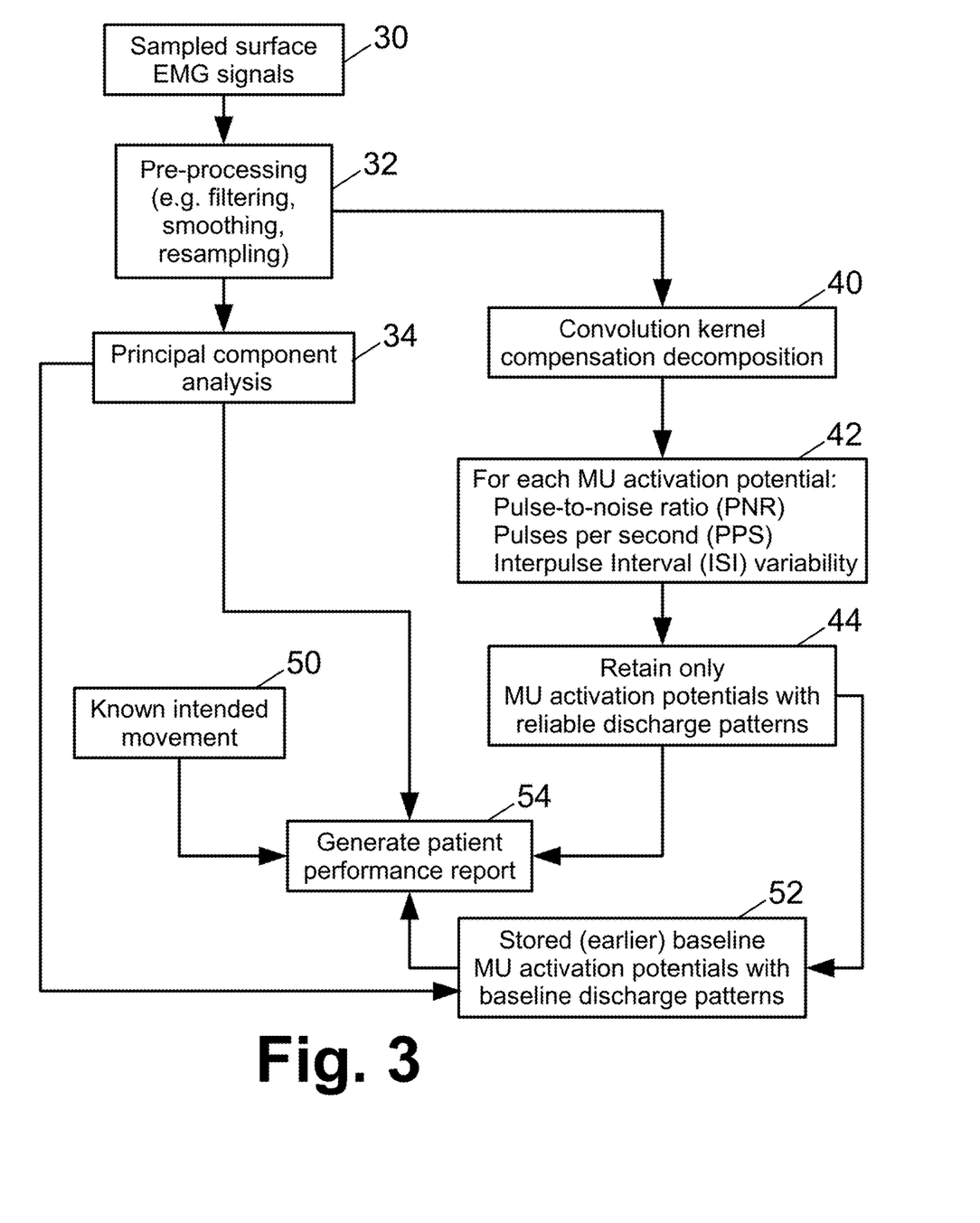
FIG. 3 diagrammatically illustrates a variant method suitably performed by a diagnostic controller and the sleeve of the device of FIG. 1 for assessing performance of an SCI, stroke, or other patient with motor debilitation.

The MU action potentials-based electronic controller 20 is suitably implemented as an electronic device comprising an electronic processor 22 (e.g. a microprocessor or microcontroller or combination of microprocessors and/or microcontrollers) operatively connected with the electrodes 12 and that reads and executes instructions (e.g. software or firmware) stored on a non-transitory storage medium 24 (e.g. a hard disk drive or other magnetic storage medium and/or a flash memory or solid state drive, SSD, or other electronic storage medium and/or an optical disk or other optical storage medium, various combinations thereof, or so forth) to perform the operations as described herein (e.g. with reference to FIG. 2 for FES control embodiments, and/or FIG. 3 for diagnostic embodiments). In other words, the electronic controller 20 is programmed to perform the process of FIG. 2, and/or the process of FIG. 3, and/or variants thereof. The electronic controller 20 further includes analog-to-digital (A/D) circuitry and optionally other electronics (e.g. an amplifier) for receiving and digitizing the surface EMG signals (generically indicated by element 26 in FIG. 1); and a pulse generator 28 for generating FES pulses to be delivered to the electrodes 12. The electronic controller 20 may be integrated into the wearable electrodes garment 10 (e.g. as a small shielded module secured to the exterior of the electrodes garment 10), or may be a belt-worn electronics module connected with the electrodes garment 10 by a wire bundle or cable (optionally connecting via a detachable electrical connector such as a plug, socket, or so forth) or by a Bluetooth or other wireless connection, or may be a desktop computer or the like (in which case patient mobility when wearing the connected electrodes garment is limited).

With reference now to FIG. 2, an illustrative example of a method suitably performed by the electronic controller 20 is described. In the method, the electronic controller 20 receives surface EMG signals 30, which are assumed to be in digital form (e.g. processed by the A/D 26). As previously noted, the surface EMG signals 30 are predominantly electrical activity produced by skeletal muscles, but also include MU activation potentials as a substantially weaker component. In an operation 32, pre-processing such as filtering, smoothing, resampling, or the like is performed to condition the surface EMG signals 30 for further processing. (It is contemplated for some of this preprocessing to be performed in the analog domain prior to the ND 26). In one non-limiting illustrative example, the surface EMG signals are sampled at 30 kHz, bandpass filtered (e.g. with a passband of around a few Hertz to around 7500 Hz or narrower in some embodiments) and resampled at 3 kHz. The preprocessing 32 may also remove FES-induced artifacts. The FES not only causes the muscles to contract, it also creates an artifact that becomes present in the EMG data. This artifact includes a brief period of hardware saturation, followed by an M-wave (response of muscles due to extreme depolarization from FES), followed by an H-wave (response due to the H-reflex). This artifact is suitably removed as part of the preprocessing 32.

The resulting pre-processed surface EMG signals are then processed to generate features drawn from the surface EMG signals (neglecting the impact of the much weaker MU action potentials) and to extract the much weaker MU action potentials which are then also characterized by selected features.

In a non-limiting illustrative example of FIG. 2, the pre-processed surface EMG signals undergo principal component analysis (PCA) 34 and the one, two, three, or possibly more most discriminative (i.e. most principal) components output by the PCA 34 serve as features representing the EMG signals. Additionally, one or more regions of high neural activity 36 may be identified which can provide gross anatomical information useful for identifying the movement.

With continuing reference to FIG. 2, a convolutional kernel compensation (CKC) decomposition 40 is performed on the pre-processed surface EMG signals to generate one or more MU activation potentials. The CKC decomposition is an illustrative example, and more generally other approaches such as Wavelet decomposition can be employed for decomposing EMG and extracting MU activity. See Wang et al., "The Analysis of Surface EMG Signals with the Wavelet-Based Correlation Dimension Method", Computational and Mathematical Methods in Medicine Volume 2014, Article ID 284308 (2014); Li et al., "Wavelet-based detection on MUAPs decomposed from sEMG under different levels of muscle isometric contraction", Proc. of 2017 IEEE International Conference on Robotics and Biomimetics (ROBIO) (2017); Wei et al., "A Wavelet-Based Method to Predict Muscle Forces From Surface Electromyography Signals in Weightlifting", Journal of Bionic Engineering vol. 9 issue 1 pages 48-58 (March 2012). In an operation 42, for each MU activation potential, suitable characteristics (i.e. features) are computed. In the illustrative examples, these include: a discharge rate, specifically in the illustrative examples a mean firing rate (i.e. mean discharge rate) in pulses per second (pps); the Interpulse Interval (ISI) variability in a percentage value; and the Pulse-to-Noise Ratio (PNR) in dB. Optionally, only one or two of these three illustrative characteristics are computed, and/or one or more other characteristics are computed. The choices of units (pps, %, dB) are also illustrative examples and the characteristics may be expressed in other suitable units. In an operation 44, only those MU activation potentials which exhibit a reliable discharge pattern (as indicated by one or more of the characteristics computed in operation 42) are retained. It will be appreciated that the output of the second path via the operation 44 includes (at least) an identification of a set of one or more MUs and the discharge (i.e. firing) rate for each identified MU.

In an operation 46, the features presenting the EMG information (e.g. from the illustrative principal components analysis 34, optionally along with the identified region(s) of high neural activity 36) and the features representing the reliable MU activation potentials (from operations 42, 44) are combined to identify the intended movement. In one approach, the identified region(s) of high neural activity 36 is used to apply a region-specific movement classifier that receives as input the EMG and MU activation potential(s) features (e.g., the principal components from the principal components analysis 34 and the number of MU activation potentials and discharge rates for these as output by the operation 44). More generally, various anatomical regions are associated with movement models parameterized by EMG information and MU activation potential(s) information. The output of the region-specific movement classifier(s) is the identification of the intended movement. By way of some nonlimiting illustrative examples, the region-specific movement classifier(s) may be (optionally multinomial) logistic regression classifiers, SVM classifiers, ANNs, or other ML component(s) that are pre-trained by having the patient (or a cohort of similar patients) perform various volitional movements while measuring surface EMG signals and processing via operations 40, 42, 44 to generate MU activation potential(s) information labeled by the known intended movements that is then used to train the ML component(s) to provide the pre-trained anatomical part-specific movement classifier(s).

In an operation 48, the FES control signals appropriate to implement the intended movement identified in the operation 46 are determined. This can employ the same type of processing employed in brain-computer interface (BCI) driven FES, except that here the input intended movement in provided by the processing/information 32, 34, 36, 40, 42, 44 of FIG. 2 rather than being provided by intracortical data acquired and decoded by a BCI. The output of the operation 46 is used to operate the pulse generator 28 to generate desired FES pulses that are applied by the electrodes 12.

With reference to FIG. 3, in a variant embodiment, the wearable electrodes sleeve or other garment 10 is used as a diagnostic device, rather than for delivery of FES. In other words, in this variant embodiment the electrodes 12 of the electrodes sleeve 10 are used to acquire the surface EMG signals 30, but are not used to deliver FES to the body part. As such, in this variant embodiment the pulse generator 28 of FIG. 1 can be omitted from the electronic controller 20. As shown in FIG. 3, the electronic controller 20 of this variant embodiment performs the analyses 32, 34, 40, 42, 44 of the sampled surface EMG signals 30 as described with reference to FIG. 2. However, for diagnostic purposes, these analyses are performed on the sampled surface EMG signals 30 acquired while the patient is performing (or attempting/ intending to perform) a known intended movement 50. For example, the patient may be asked to touch an object using the index finger, and the surface EMG signals 30 are acquired and analyzed while the patient is performing (or attempting to perform) the action of touching the object using the index finger. Since the intended movement 50 is known, the region identification 36 and the movement identification 46 of the FES delivery embodiment of FIG. 2 are omitted in the diagnostic device of FIG. 3. Instead, the resulting EMG features and the reliable MU activation potentials and corresponding discharge patterns output by the operations 32, 34, 40, 42, 44 are compared with corresponding baseline EMG features and MU activation potentials and baseline discharge patterns 52 for the known intended movement 50. The baseline values 52 are suitably baseline values obtained for the patient in an earlier session. (Accordingly, the presently acquired EMG and MU values are stored in the storage 52 for possible use as a baseline in a subsequent session). Based on the comparison of the current EMG and MU values with the baseline values, a patient performance report 54 is generated for the intended movement 50. In general, the goal of rehabilitation therapy is to observe improvement in the current session compared with the baseline performance 52, and this improvement (or lack of improvement; or degradation in performance compared with the baseline if this is indeed the case) is summarized in the patient performance report 54. The report may also provide trendlines of the performance over a series of sessions so as to graphically represent patient performance over time. In a variant embodiment, the movement identification 46 is omitted, and the generation of the performance report 54 is based only on the comparison of the extracted MU action potentials versus the baseline MU action potentials.

In another diagnostic approach (not shown), expected MU activation potentials with expected discharge patterns are suitably obtained by performing the diagnostic process on healthy patients (e.g., patients who do not have SCI, stroke, or otherwise-produced debilitation of the index finger). The report 54 then provides metrics of how closely the patient's performance, as measured by the EMG information and the reliable MU activation potentials (e.g. the number of recruited MUs) and their characteristics (e.g. PNR, discharge rate, ISI variability of the reliable MU activation signals) matches up with the expected MU activation potentials and expected characteristics. This assessment approach can be used instead of, or in addition to, the illustrated comparison with baseline values 52 from an earlier session.

In some embodiments (including the illustrative embodiments), the therapeutic or diagnostic device does not include a brain-computer interface (BCI), and does not employ intracortical signals in performing the FES therapy or patient performance diagnostics. Alternatively, in other embodiments it is contemplated to augment the MU actions potential and EMG information obtained as disclosed herein with intracortical signals acquired by a suitable intracortical electrode or electrodes array.

In the following, some experimental testing relating to aspects of this disclosure are described.

The study participant was a 32 year old male with a C5 motor and C6 sensory American Spinal Injury Association Impairment Scale B spinal cord injury sustained 14 years prior to the experiment. Data were collected as part of an ongoing intracortical brain-computer interface trial conducted under and FDA Investigational Device Exemption and approved by the University of Pittsburgh Institutional Review Board (NCT01894802). Informed consent was obtained prior to any experimental procedures. Intracortical data were not used in the experiments presented here. The participant had normal strength of the elbow flexors and was able to extend his wrist fully with gravity removed but not against gravity with resistance. He had no volitional movement of the elbow extensors, wrist flexors, finger flexors, or finger abductors.

The participant was seated in front of a monitor and cued to attempt a series of movements involving the digits, hand, wrist, and elbow. Specifically, the subject was instructed to flex/extend each digit, close/open his hand, flex/extend and pronate/supinate his wrist, and flex/extend his elbow.

A sleeve electrode array (Battelle Memorial Institute, Columbus, Ohio) containing 150 electrodes was used to measure EMG activity in the extensor and flexor muscles of the forearm during each of the movement trials (FIG. 1, upper and middle drawings D1 and D2). The electrodes were 12 mm diameter stainless steel discs with an interelectrode distance of approximately 15 mm, spanning from the wrist to the elbow joint. Monopolar EMG signals were sampled at 30 kHz. EMG signals were bandpass filtered (3rd order zero-lag Butterworth digital filter, pass-band 10-500 Hz) and resampled at 3000 Hz. Two (open) channels were removed before further processing.

Classification of five digit tasks was performed using the filtered and smoothed EMG signals across all 150 channels of the electrode array. For this analysis, the raw EMG signals were band-pass filtered (zero-lag 4th-order Butterworth digital filter, pass-band 75-7500 Hz), smoothed (zero-lag 4th order Butterworth digital filter, cutoff frequency 10 Hz), and resampled at 3000 Hz. Principal component analysis (PCA) was performed on the smoothed signal across channels, and two components were found to account for >95% of the variance and used for classification. Multinomial logistic regression was used to classify movements of the five digits over eight movement periods per digit with leave-one-out cross-validation. One set from each fold was used for testing and the remaining seven sets were used for training. This corresponds to a specific embodiment of the operations 32, 34, 36, of FIGS. 2 and 3.

EMG signals were decomposed into the constituent trains of MU action potentials using the convolution kernel compensation algorithm. Only MUs that showed reliable discharge patterns were selected for the analysis. Spike trains were then represented as binary signals. The spike trains extracted from the EMG were used to trigger a bidimensional average of the global surface EMG to extract the MU action potential waveforms for each channel of the grids. After the blind source separation, we further tested the accuracy of the decomposition by checking the individual MU action potential visually. This analysis was performed by an experienced investigator. This corresponds to a specific embodiment of operation 40 of FIGS. 2 and 3, with the selection of only MUs that showed reliable discharge patterns for the analysis corresponding to operation 44 of FIGS. 2 and 3.

Neural connectivity analysis was performed by computing the coherence function between motor neuron discharge timings. From this analysis, common oscillations in the beta band (>20 Hz) are believed to arise from cortical neurons, and the peak at 10 Hz has been related to the tremor frequency, whilst the lower band reflects the effective neural drive to the muscle (<5 Hz). The coherence functions were computed from non-overlapping 1-s Hanning windows. The coherence (C) was averaged across 50 permutations of motor units and transformed to standard z score. For this purpose, we first converted the coherence in Fishers value $FZ=a \tan h(C)$. This value was then normalized to the number of segments (L) used to calculate the coherence $Z=FZ/(\frac{1}{2}L)$ which corresponds to the variance of estimation. The coherence bias was identified as the average coherence value in the frequency range 100-250 Hz.

Estimates of synaptic noise to motor neurons were obtained by computing the variability in the motor unit interpulse intervals (ISIs). ISI variability was the average motor unit ISI divided by the ISI standard deviation for each motor unit. This value was then averaged across all motor units. The results are presented in the "ISI variability (%)" column of the table of FIG. 4.

Figure 5:
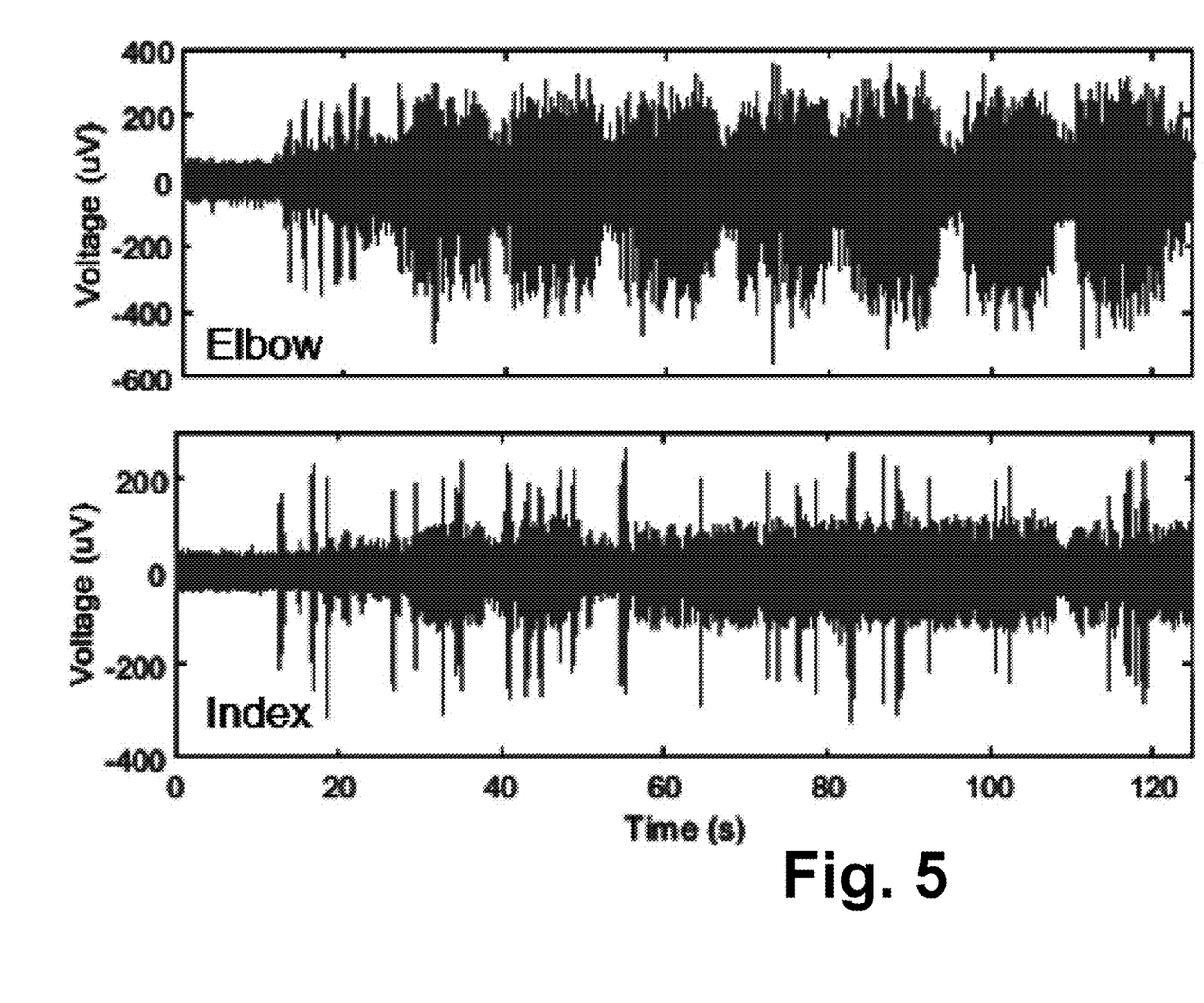

We recorded discernible EMG activity in the paralyzed forearm of an individual with SCI despite a lack of observed movement in the fingers and hand during the tasks. FIG. 5 shows the band-pass filtered EMG signal on a single channels for elbow flexion and extension (top plot of FIG. 5) and index flexion and extension (bottom plot of FIG. 5). The movement periods are easily discriminated from rest during the elbow trial while attempted movements of the index finger are difficult to distinguish visually. However, this myoelectric activity, with minimal post-processing, was robust enough to allow for successful discrimination of all five fingers during attempted flexion and extension movements. It should be noted that the subject attempted the motions for which EMG activity are reported in FIG. 5 without generating detectable motion.

Figure 6:
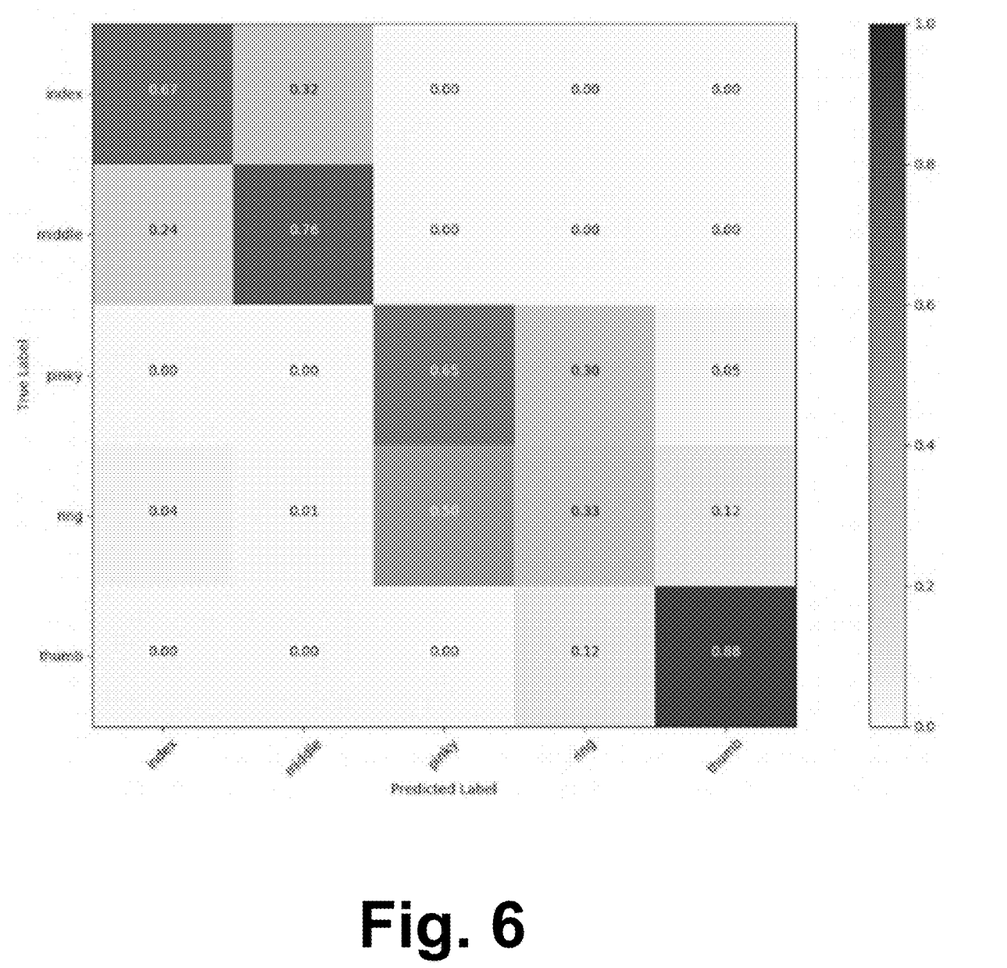

The classification results are shown in FIG. 6, where classification of five digit tasks was performed using multiple linear regression with leave-one-out cross-validation used to classify attempted movements of the five digits during eight movement periods per digit. The accuracy of each decoded movement was calculated as the proportion of samples classified correctly out of all samples of the movement. Thumb finger trials were classified with the highest accuracy (88%), followed by middle (76%), index (67%), pinky (65%), and, lastly, ring (33%). The digits most often confused were ring and pinky and index and middle. A one-sided T-test with alpha 0.05 showed that the classification performs significantly better than chance (p=0.0037). In this step, we have demonstrated that movements can be decoded from residual EMG activity in the absence of visual movement, likely due to the high sensor count across the forearm. It is expected that the electrode sleeve's high channel density and large coverage area will also allow for the classification of more complex hand movements, for example using the MU information gathered in operations 40, 42, 44 of FIGS. 2 and 3. While decoding movements is necessary for the control of neuroprosthetics and assistive devices (e.g., the therapeutic method of FIG. 2), the analysis of extracted MU activity can provide a more thorough description of the physiological changes after neurological damage and throughout the recovery process (e.g., the diagnostic method of FIG. 3).

Figure 4:
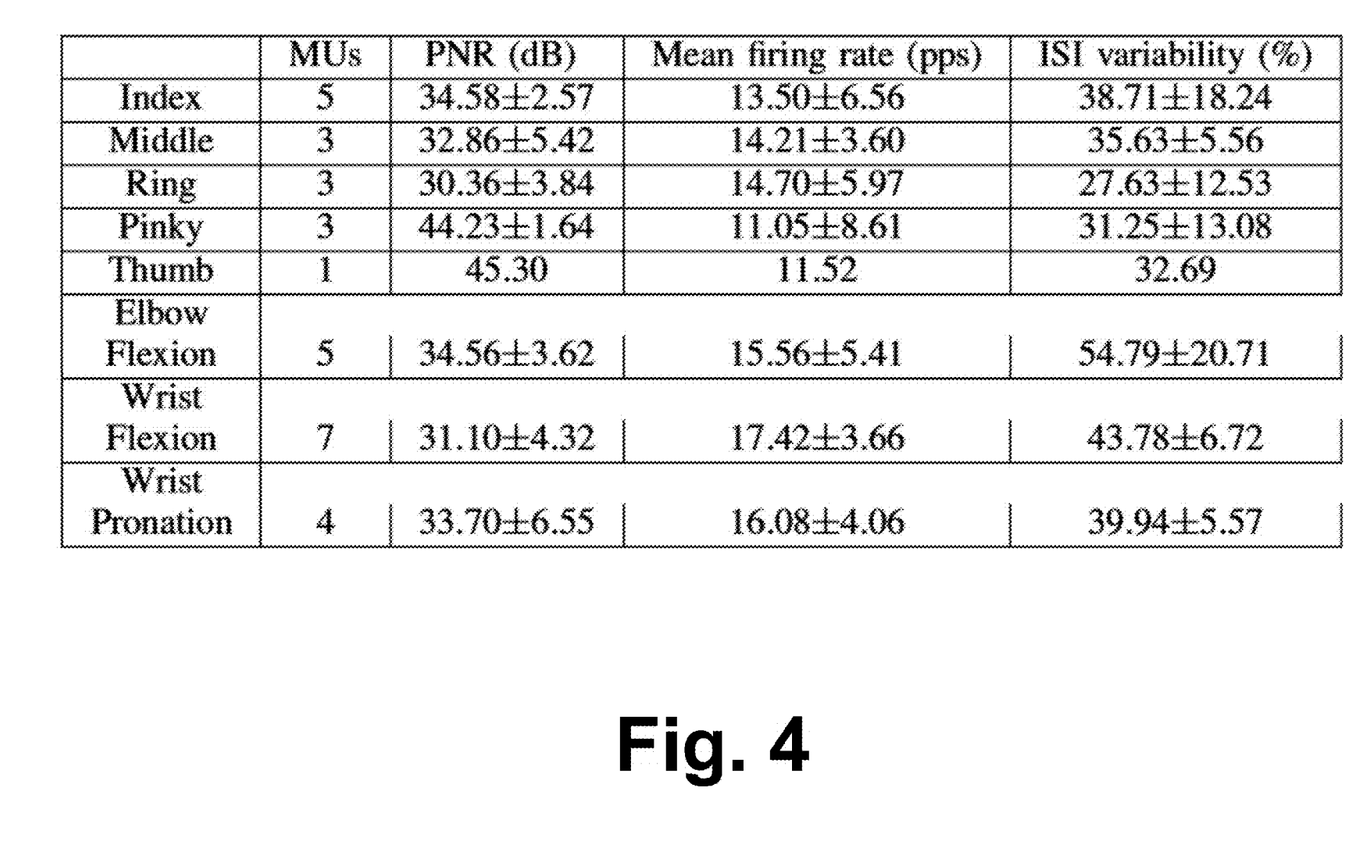
FIGS. 4-9 present experimental results as described herein.

With returning reference to the table of FIG. 4, the "MUs" column reports the number of identified motor units (MUs) during the individual digit tasks and joint movements. We identified the activity of a relatively large population of motor units. The pulse-to-noise ratio (PNR), average discharge rate, and the interspike interval variability is shown in the "PNR (dB)", "Mean firing rate (pps)", and "ISI variability (%)" columns of the table of FIG. 4, respectively. The computing of these characteristics of the MU action potentials corresponds to a specific embodiment of the operation 42 of FIGS. 2 and 3.

Figure 7:
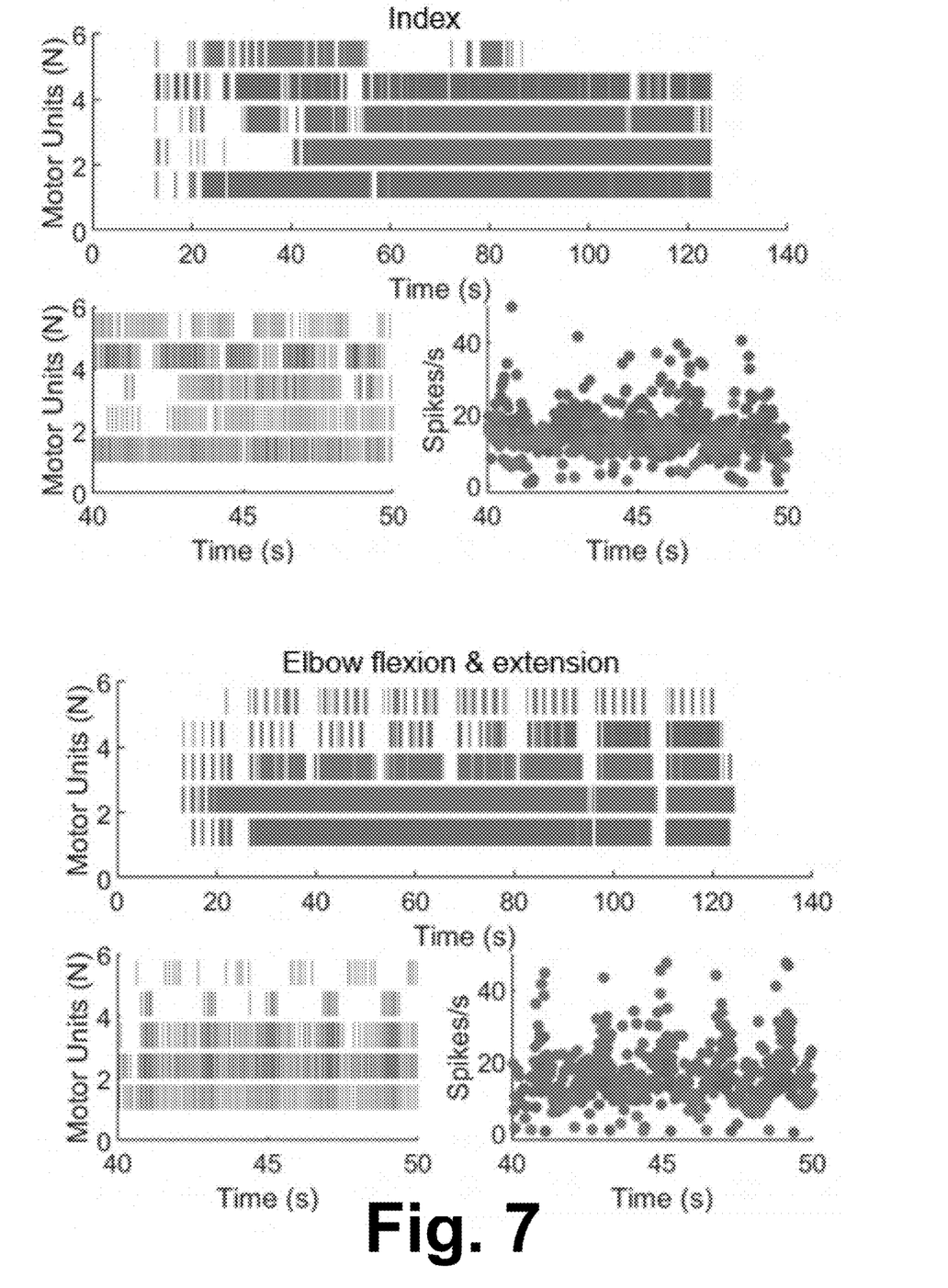
Figure 8:
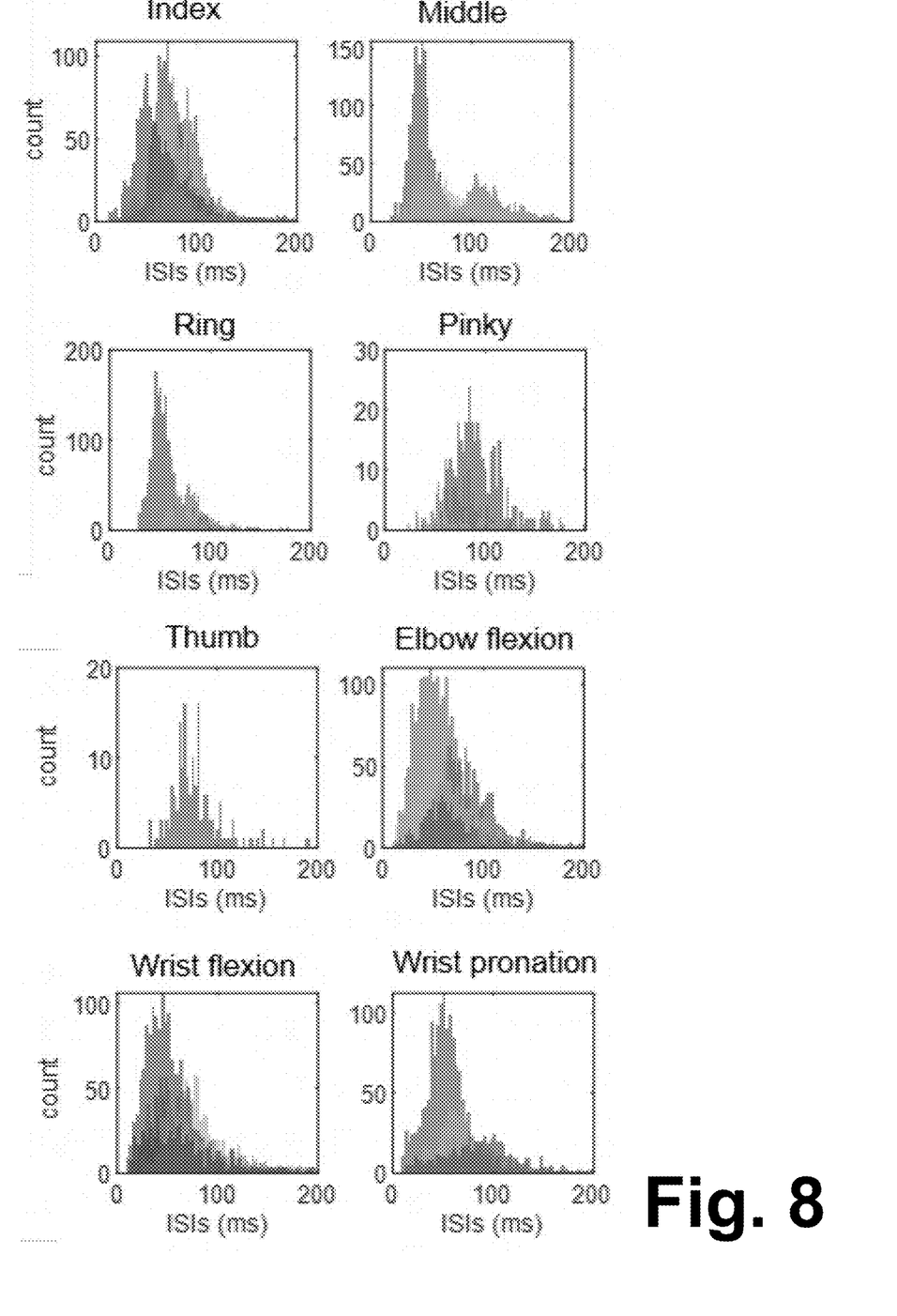
Figure 9:
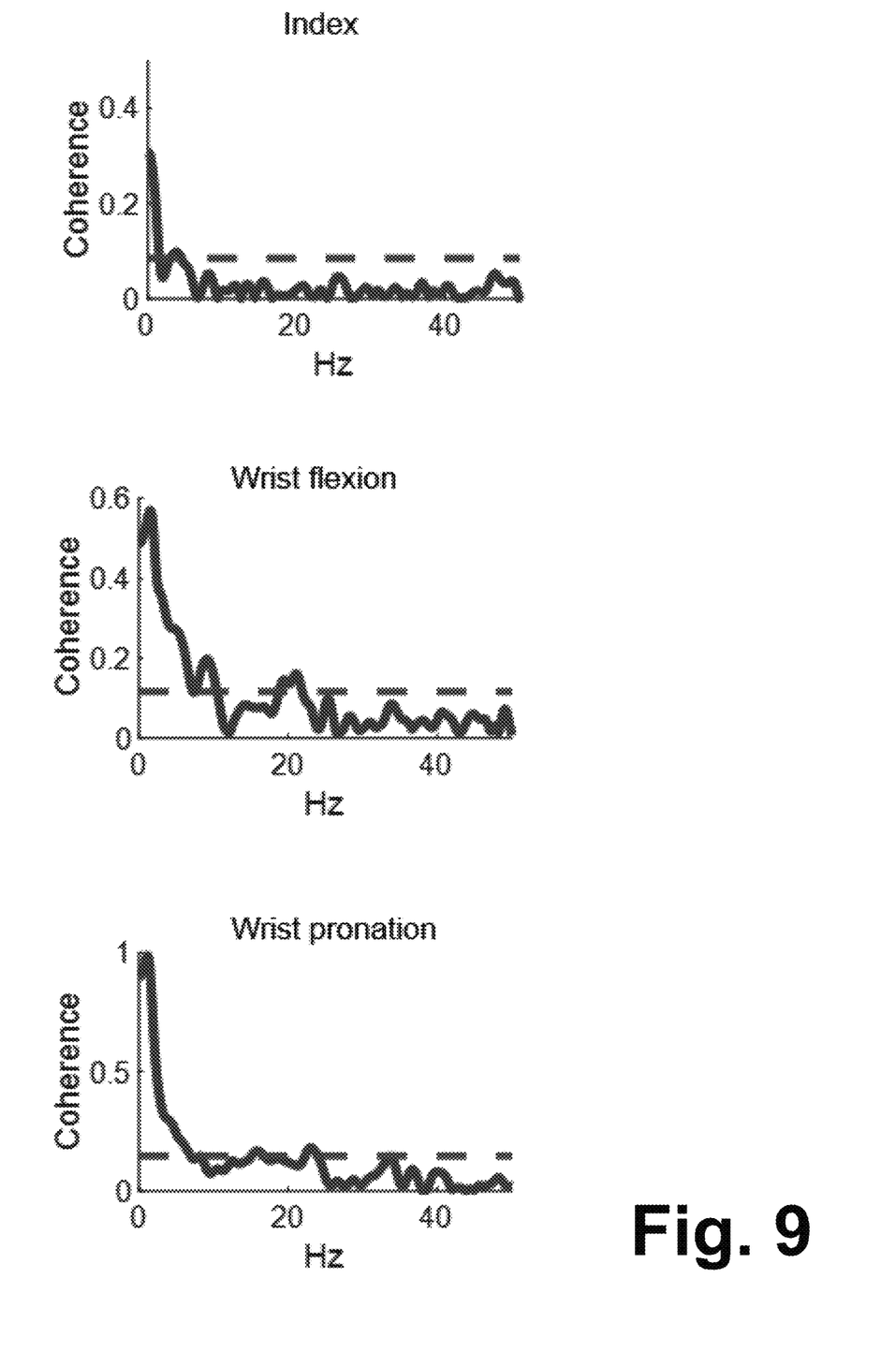

FIGS. 7, 8, and 9 present extracted MU activity in graphical formats, and show the extracted motor unit spike instants for two representative movement trials, index flexion and extension and elbow flexion and extension. Interestingly, some motor units showed a tonic activity whilst other were activated in bursts during the dynamic tasks, reflecting common strategies of joint movements as in intact individuals. Moreover, The average discharge rate and the interspike intervals (see table of FIG. 4) showed similar values as those that have been observed in healthy subjects.

However, the discharge rate variability was significantly higher than what has been observed in healthy individuals (see table of FIG. 4; average across conditions 38.05±8.50%) which may indicate an increase in synaptic noise.

The common input to motor neurons was assessed only for the tasks where we identified greater than three motor units. During wrist flexion and extension, the joint movement with the highest number of identified motor units (number of MUs=7), we observed strong common oscillations in the delta and beta band. These findings indicate that following spinal cord injury (SCI), motor neurons still receive common inputs in the effective bandwidth for force generation (delta band) and receive cortical oscillations common to the pool (beta band).

In some contemplated variants, more complex hand movements may be similarly classified, such as multiple grasp types, and proportional control of those movements with a comparison of input features from both the composite EMG signal and the decomposed MU activity. For example, as noted previously, a higher number of identified MU units with higher discharge rates is expected to correspond to a higher force (albeit possibly with coarser control) intended action; whereas, a smaller number of MU units with lower discharge rates is expected to correspond to a more precisely controlled, lower force intended action It is further contemplated to leverage analysis of the spiking activity recorded in the motor cortex during the movement tasks (in embodiments in which intracortical activity is recorded, e.g. via an intracortical electrode or electrodes array) for comparison to the decomposed MUs recorded in the musculature.

The described experiments demonstrate that myoelectric activity can be detected and decoded from the forearm of a person with tetraplegia without motion of the hand or fingers, providing a robust control signal for neuroprosthetics and other assistive technologies. This EMG activity can be decomposed into individual MUs, which can provide insight into spinal network reorganization and recovery following neurological injuries, such as SCI and stroke.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An electromyography device comprising:
a wearable electrodes garment including electrodes disposed to contact skin when the wearable electrodes garment is worn;
an electronic controller operatively connected with the electrodes and programmed to perform a method including:
receiving surface electromyography (EMG) signals via the electrodes;
extracting one or more motor unit (MU) action potentials from the surface EMG signals wherein each MU comprises a motor neuron and skeletal muscle fibers innervated by that motor neuron and each MU action potential comprises the electrical signal carried by the motor neuron of the corresponding MU and wherein the extracting of the one or more MU action potentials from the surface EMG signals includes computing one or more features of each MU action potential and retaining only those of the one or more MU action potentials which exhibit reliable discharge patterns as indicated by one or more of the features; and
at least one of:
(i) identifying an intended movement based at least on features representing the one or more extracted MU action potentials and delivering functional electrical stimulation (FES) effective to implement the intended movement via the electrodes of the wearable electrodes garment or
(ii) generating a performance report based at least on a comparison of features representing the one or more extracted MU action potentials and features representing expected and/or baseline MU action potentials for a known intended movement.

2. The electromyography device of claim 1 wherein:
the method further includes identifying at least one region of high neural activity based on the surface EMG signals,
wherein the intended movement is identified based on the at least one region of high neural activity and the features representing the one or more extracted MU action potentials.

3. The electromyography device of claim 2 wherein the identifying of the intended movement includes applying one or more movement classifiers specific to the identified at least one region of high neural activity to the features including at least the features representing the extracted one or more MU action potentials to identify the intended movement by classifying the movement using the one or more movement classifiers.

4. The electromyography device of claim 3 wherein the features representing the one or more extracted MU action potentials include a number of MU activation potentials and discharges rates for the MU activation potentials.

5. The electromyography device of claim 2 wherein a classifier is applied to features including at least one or more principal components of the surface EMG signals extracted by principal component analysis (PCA).

6. The electromyography device of claim 1 wherein the extracting of one or more MU action potentials from the surface EMG signals includes performing a convolutional kernel compensation (CKC) decomposition on the surface EMG signals to extract the one or more MU activation potentials.

7. The electromyography device of claim 1 wherein the one or more features include one or more features of the group consisting of: a discharge rate; an Interpulse Interval (ISI) variability; and a Pulse-to-Noise Ratio (PNR).

8. The electromyography device of claim 1 wherein the method includes (i) identifying an intended movement based at least on features representing the one or more extracted MU action potentials and delivering functional electrical stimulation (FES) effective to implement the intended movement via the electrodes of the wearable electrodes garment.

9. The electromyography device of claim 1 wherein the method includes (ii) generating a performance report based at least on a comparison of features representing the one or more extracted MU action potentials and features representing expected and/or baseline MU action potentials for a known intended movement.

10. The electromyography device of claim 1 wherein the wearable electrodes garment includes at least 50 electrodes disposed to contact skin when the wearable electrodes garment is worn.

11. The electromyography device of claim 1 wherein the wearable electrodes garment is a wearable electrodes sleeve.

12. An electromyography device comprising:
a wearable electrodes garment including electrodes disposed to contact skin when the wearable electrodes garment is worn;
an electronic controller operatively connected with the electrodes and programmed to perform a method including:
receiving surface electromyography (EMG) signals via the electrodes;
extracting one or more motor unit (MU) action potentials from the surface EMG signals wherein each MU comprises a motor neuron and skeletal muscle fibers innervated by that motor neuron and each MU action potential comprises the electrical signal carried by the motor neuron of the corresponding MU, wherein the extracting of the one or more MU action potentials from the surface EMG signals includes computing one or more features of each MU action potential and retaining only those of the one or more MU action potentials which exhibit reliable discharge patterns as indicated by one or more of the features;
identifying an intended movement based on features including at least features representing the one or more extracted MU action potentials; and
delivering functional electrical stimulation (FES) effective to implement the intended movement via the electrodes of the wearable electrodes garment.

13. The electromyography device of claim 12 wherein the one or more features include one or more characteristics of the group consisting of: a discharge rate; an Interpulse Interval (ISI) variability; and a Pulse-to-Noise Ratio (PNR).

14. The electromyography device of claim 12 wherein the identifying of the intended movement is further based on features comprising one or more principal components of the surface EMG signals extracted by principal component analysis (PCA).

15. The electromyography device of claim 12 wherein the identifying of the intended movement includes applying one or more movement classifiers specific to a region of high neural activity identified based on the EMG signals to the features to identify the intended movement by classifying the movement using the one or more movement classifiers.

16. The electromyography device of claim 12 wherein the features representing the one or more extracted MU action potentials include a number of the one or more extracted MU action potentials, and discharges rates for the one or more MU activation potentials.

17. The electromyography device of claim 12 wherein the wearable electrodes garment includes at least 50 electrodes disposed to contact skin when the wearable electrodes garment is worn.

18. The electromyography device of claim 12 wherein the therapeutic device does not include a brain-computer interface (BCI).

19. An electromyography method comprising:
receiving surface electromyography (EMG) signals via electrodes of a wearable electrodes garment; and
using an electronic processor:
extracting one or more motor unit (MU) action potentials from the surface EMG signals wherein each MU comprises a motor neuron and skeletal muscle fibers innervated by that motor neuron and each MU action potential comprises the electrical signal carried by the motor neuron of the corresponding MU, wherein the extracting of the one or more MU action potentials from the surface EMG signals includes computing one or more features of each MU action potential and retaining only those of the one or more MU action potentials which exhibit reliable discharge patterns as indicated by one or more of the features; and
one of:
(i) identifying an intended movement based at least on the one or more extracted MU action potentials and delivering functional electrical stimulation (FES) effective to implement the intended movement via the electrodes of the wearable electrodes garment or
(ii) generating a performance report based at least on a comparison of the one or more extracted MU action potentials and expected and/or baseline MU action potentials for a known intended movement.

\* \* \* \* \*